United States Patent [19]

Matthews et al.

[11] Patent Number: 4,706,659

[45] Date of Patent: Nov. 17, 1987

[54] FLEXIBLE CONNECTING SHAFT FOR INTRAMEDULLARY REAMER

[75] Inventors: Larry S. Matthews; Steven A. Goldstein, both of Ann Arbor, Mich.

[73] Assignee: Regents of the University of Michigan, Ann Arbor, Mich.

[21] Appl. No.: 678,682

[22] Filed: Dec. 5, 1984

[51] Int. Cl.⁴ .............................................. A61F 5/04
[52] U.S. Cl. ................................. 128/92 VD; 128/83; 464/173; 464/179; 464/57
[58] Field of Search ................. 128/92 E, 83; 464/19, 464/173, 179, 57

[56] References Cited

U.S. PATENT DOCUMENTS

| 8,231 | 5/1878 | Hartman | 464/173 |
|---|---|---|---|
| D. 235,107 | 5/1975 | Adler | D24/1 B |
| D. 239,131 | 3/1976 | Adler | D54/13 A |
| 1,200,216 | 10/1916 | Monard | 464/179 |
| 1,314,600 | 9/1919 | McCaskey | 464/179 |
| 2,717,146 | 9/1965 | Zublin | 464/19 |
| 3,203,285 | 8/1965 | Schmidt | 81/177 |
| 3,554,192 | 1/1971 | Isberner | 128/83 |
| 4,362,520 | 12/1982 | Perry | 464/179 |
| 4,473,070 | 9/1984 | Matthews et al. | 128/92 E |

FOREIGN PATENT DOCUMENTS 241255   7/1946   Switzerland ...................... 464/149

Primary Examiner—Robert Peshock
Assistant Examiner—Wenceslao J. Contreras
Attorney, Agent, or Firm—Sherman and Shalloway

[57] ABSTRACT

Disclosed herein are embodiments of a flexible connecting shaft for an intramedullary reamer. In each embodiment, several short segments or links are attached together to form an elongated flexible shaft which shaft is designed, due to the specific attachment means for the links, to bend along its longitudinal axis while transmitting torque without any lag in such transmission. A link at one end of the flexible shaft as made by a plurality of the links includes means provided for attachment to a torque providing device such as an electric motor. At the opposite end of the shaft, the last link includes structure thereon enabling connection to a drill bit. The various embodiments disclose different ways of interconnecting the links.

4 Claims, 11 Drawing Figures

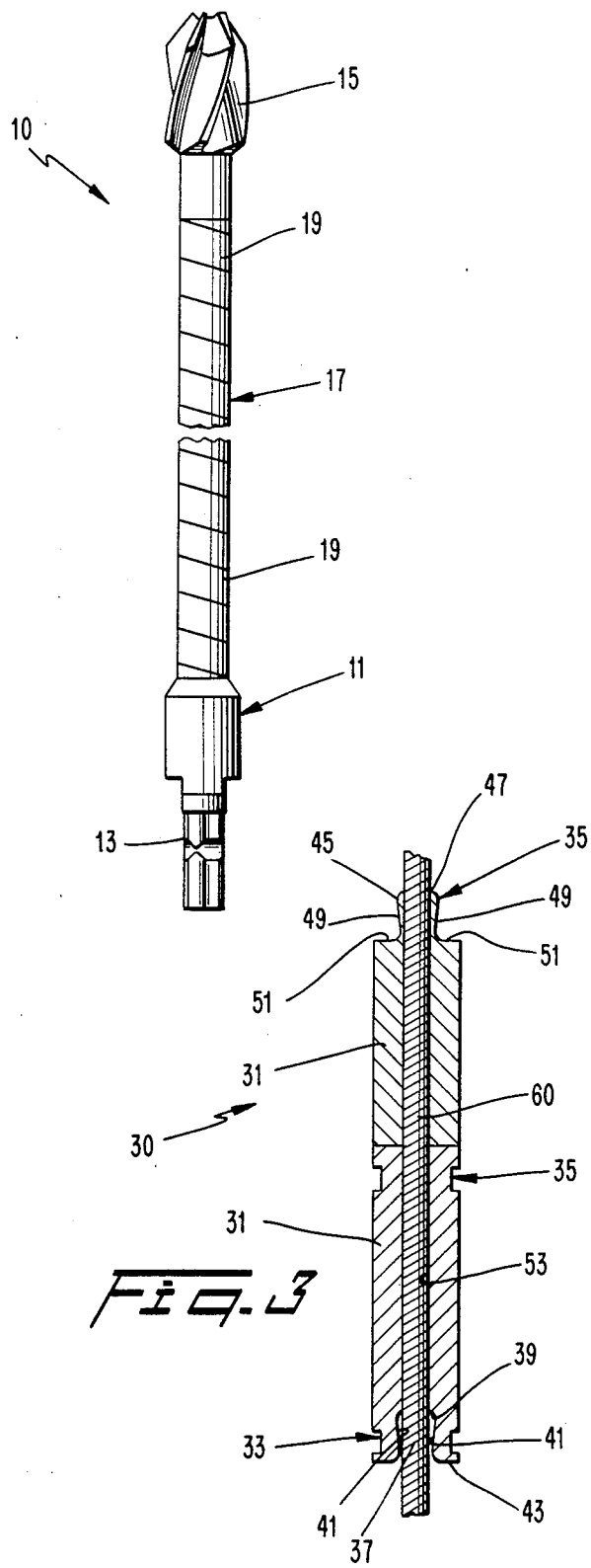
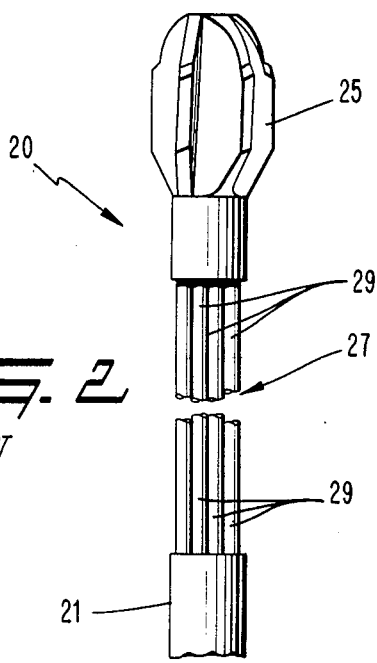
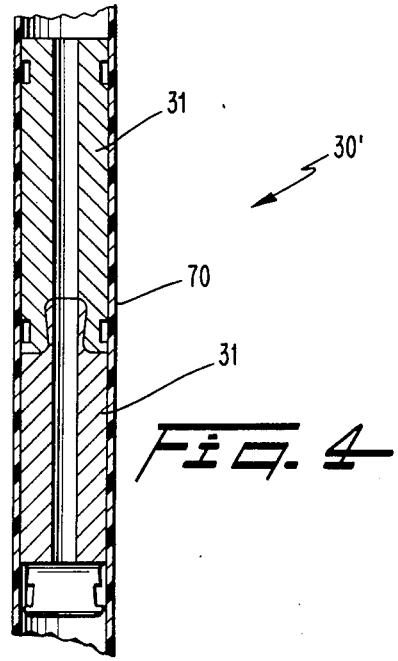

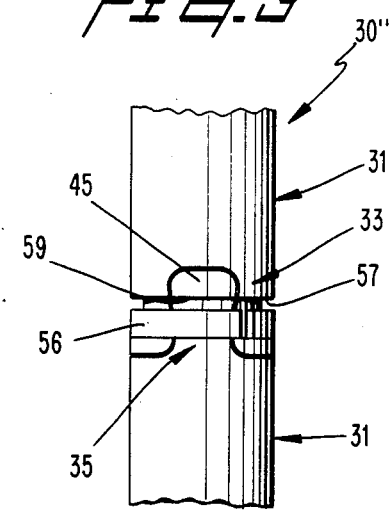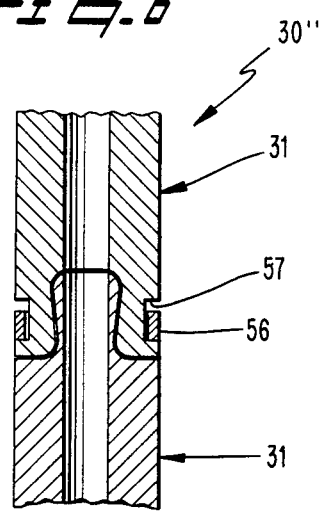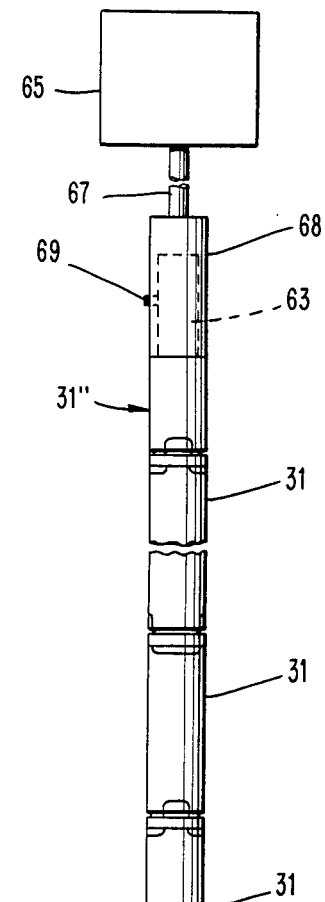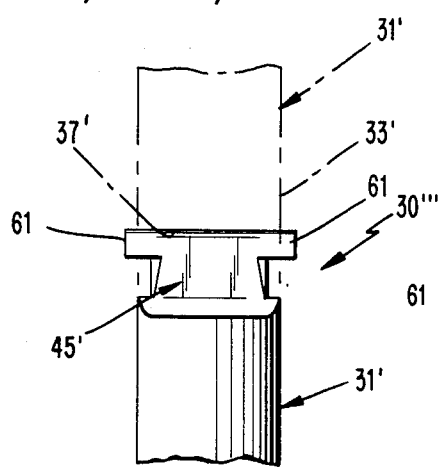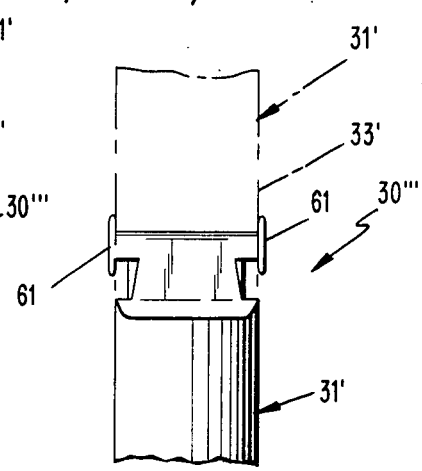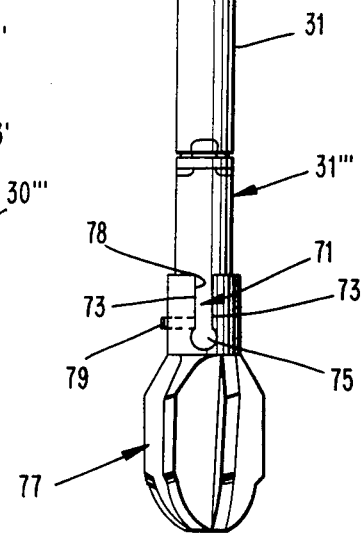

4,706,659

FLEXIBLE CONNECTING SHAFT FOR INTRAMEDULLARY REAMER

BACKGROUND OF THE INVENTION

Many fractures of long bones can be satisfactorily stabilized by the surgical insertion of a shaft, rod or nail into the intramedullary canal of the bone. Since the natural canal is irregular in internal diameter and configuration from end to end, and since all intramedullary fixation devices gain strength with increases in diameter, most surgical procedures call for incremental reaming with sequentially used reamers having 0.5 mm or 1.0 mm inmcreases in outside diameter. Because the shafts of most long bones are bent or curved along their longitudinal axes, flexible shafts that can bend to follow this naturally curved path while transmitting torque are necessary in the art of intramedullary reaming so as to prevent the reamer from cutting through the wall or cortex of the bone. If the reamer shaft is inflexible and thereby does not follow the natural curvature of the bone, the reamer head may in fact cut through the wall or cortex of the bone being reamed.

Presently marketed flexible intramedullary reamer shafts are designed in such manner that they store rotational energy in a spring manner whenever the cutting head stops or gets caught by the bone structure. When this happens, the driving motor continues to turn the proximal end of the shaft to thereby increase the torque and to thereby store energy in the shaft until the force exerted by the shaft exceeds the force which is retaining the cutter head. At this point, the cutter head becomes dislodged thereby allowing the release of the stored rotational energy so that the cutter head springs, jumps, or spins ahead rapidly in an uncontrollable fashion within the bone. In many cases, the above described scenerio repeats itself over and over again to thereby cause what is known in the art as "chatter". These irregular, uncontrollable movements of the reamer head caused by the spring-like shaft may damage the bone and act to greatly increase the risks of surgical complications. Two examples of prior art constructions exhibiting the above described characteristics are illustrated herein in FIGS. 1 and 2 respectively, and will be described in greater detail hereinafter.

One particular problem occurs frequently in the prior art shaft shown in FIG. 1. This shaft may only be used in a forward rotational direction since if it is inadvertently or intentionally used in reverse, the spring-like shaft may unwind and virtually self-destruct. This often occurs when a surgeon attempts to reverse the rotational motion of the cutter head to dislodge it. In a further problem typical of prior art reamer shafts which are made of multiple strands of wire, cable, or strap material wrapped in a helical fashion, blood may enter the spaces between the various associated parts thereof, which blood or tissue may not be readily removed and could in fact become a danger to subsequent patients.

SUMMARY OF THE INVENTION

The present invention overcomes the deficiencies and problems evident in the prior art as described hereinabove by combining the following features into an integral longitudinally flexible and torsionally inflexible reamer shaft as follows:

(a) In each embodiment of the present invention, the flexible connecting shaft for an intramedullary reamer is comprised of a plurality of short segments or links made of a material such as stainless steel, chrome cobalt molybdenum alloy, titanium, or other metals, and configured from a polygonal or cylindrical rod.

(b) Each segment or link includes a male end and female end with each male end being specifically configured so as to interengage with the female end of an adjacent link.

(c) Each link includes a hole extending axially therethrough and when the links are fitted together with respective male ends inserted into respective female ends, the holes formed in respective links may be aligned with one another.

(d) In a first embodiment of the present invention, the links may be connected together to form a reamer shaft by inserting through the aligned holes in the individual links a flexible rod. This rod will hold the links together while allowing the flexing of the shaft about the longitudinal axis thereof.

(e) In a second embodiment of the present invention, instead of a flexible rod inserted through the aligned holes, the loosely assembled links may be inserted into an elongated flexible tube which will hold the links together while allowing the desired flexing thereof.

(f) In a third embodiment, the links may be held together with circumferentially installed securing rings. In this embodiment, the respective male and female ends of adjacent links are provided with portions of a circumferential recess which when the links are assembled to one another forms a continuous circumferential recess including portions of the respective male and female ends of the adjacent links. A securing ring is positioned around this continuous recess to thereby hold the links together while allowing the desired flexing thereof.

(g) In a further embodiment of the present invention, the links may be assembled through deformation of lateral portions of the male ends of the respective links. In this embodiment, the male ends are made slightly wider than the respective female ends so that when the links are loosely assembled to one another, the male ends slightly protrude out of the sides of the respective female ends. After loosely assembling the links together, the portions of the male ends protruding laterally outwardly from the female ends are deformed by impacting them with a tool such as a hammer so as to prevent disassembly while allowing the desired flexing of the shaft formed by the links.

Accordingly, it is a first object of the present invention to provide a reamer shaft which will flex, bend or curve to follow the natural intermedullary canal of the bone while transmitting reaming torque effectively.

It is a further object of the present invention to design a reamer shaft which will have considerable rotational or torsional stiffness so that it will not store and then irregularly release rotational energy.

It is a further object of the present invention to provide a reamer shaft which will flex, curve or bend while transmitting torque and while at the same time reaming naturally curved long bones without cutting through the cortex or side wall of the bones. It is a further object of the present invention to provide a reamer shaft which may easily be cleaned and sterilized.

It is a yet further object of the present invention to provide a reamer shaft which may be operated both in the forward and reverse directions thereof with equal effectiveness.

These and other objects, features, advantages and aspects of the present invention will be better understood with reference to the following detailed description of the preferred embodiments when read in conjunction with the appended drawing figures.

BRIEF DESCRIPTION OF THE DRAWINGS

FIG. 1 shows a side view of a first prior art construction of a reamer shaft.

FIG. 2 shows a side view of a second prior art reamer shaft.

FIG. 3 shows a cross-sectional view of a portion of the reamer shaft in accordance with the present invention with a first embodiment of link securement being shown.

FIG. 4 shows a cross-sectional view of a portion of the reamer shaft in accordance with the present invention rotated 90° with respect to the cross-section of FIG. 1 and showing a second embodiment of securement of links together.

FIG. 5 shows a side view of a portion of a reamer shaft in accordance with the present invention with a third embodiment of link securement being shown.

FIG. 6 shows a cross-sectional view through the embodiment of FIG. 5.

FIG. 7 shows a cross-sectional view of a portion of reamer shaft made in accordance with the present invention and showing a fourth embodiment of link securement specifically shown before deformation thereof.

FIG. 8 shows a view similar to the view shown in FIG. 7 but after deformation has taken place.

FIG. 9 shows a reamer shaft made in accordance with the present invention and particularly showing details of coupling means at each end thereof.

SPECIFIC DESCRIPTION OF THE PREFERRED EMBODIMENTS

Figure 10:
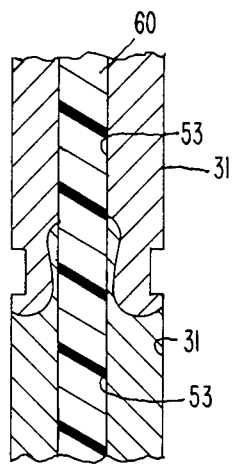
FIG. 10 shows a cross-sectional view along the line 10—10 of FIG. 3.

With reference now to FIG. 1, a first prior art construction will be described. The device 10 shown in FIG. 1 includes a connection member 11 having an end 13 provided for attachment to a drive means such as an electric motor. At the other end of the device 10, a drill bit 15 is provided so as to enable drilling of an intramedullary canal. Connecting the bit 15 and the connection means 11 is an elongated shaft 17 which is made of a long strip of metal wound in a spiral-like fashion to form coils 19 which extend throughout the longitudinal extent of the shaft 17. The shaft 17 has not been found to be an effective means of transmitting torque from the connection means 11 to the drill bit 15 since when the drill bit 15 encounters an obstruction tending to stop its motion, the shaft 17 by virtue of its coil-like construction, allows the connection means 11 to be moved by the drive motor with respect to the bit 15, to thereby enable energy to be stored up therein. When the energy stored up in the shaft 17 exceeds the forces which are retaining the bit 15 in a stationary position, the bit 15 will then jump forward which in some cases may cause damage to the structure of the bone. In another disadvantage of the prior art construction shown in FIG. 1, if the bit 15 encounters an obstruction which is not easily removed, the surgeon operating the device 10 may be tempted to reverse the direction of operation thereof to loosen the bit 15 from the obstruction. If this is done, and the bit 15 is not removed from the obstruction thereby, the reversal of the motion of the drive motor will cause the shaft 17 to uncoil, thereby ruining the shaft 17 while at the same time increasing the potential for damage to the surrounding bone tissues. In a further aspect, if sufficient reverse motion of the connection means 11 is made with respect to the bit 15, the shaft 17 might become sufficiently widened so as to prevent its extraction from the opening formed by the bit 15. Accordingly, several disadvantages in the device 10 are self-evident.

FIG. 2 shows a further prior art device designated with reference numeral 20 which is seen to include a connection means 21, a drill bit 25, and shaft means 27 interconnecting the connection means 21 and the drill bit 25. The shaft means 27 is comprised of a plurality of elongated parallel annularly disposed individual elements 29, preferably made of circular cross-section. The elements 29 are provided so as to transmit torque from the connection means 21 to the drill bit 25, however, the disadvantage of this design of shaft means 27 is that the shaft means 27 may be twisted during situations when the drill bit 25 is stuck within the intramedullary canal while the connection means 21 is still being rotated by a rotary drive means. In this situation, similarly to the FIG. 1 construction, the device 20 may buck and chatter with the shaft means 27 alternatively building up energy and releasing it to the drill bit 25. Accordingly, the use of the device 20 which is the subject of U.S. Pat. No. 3,554,192 to Isburner may prove disadvantageous.

With reference now to FIGS. 3-9, several embodiments of the present invention, each of which overcomes the disadvantages found in the prior art, will be discussed.

With reference first to FIG. 3, a portion of the shaft 30 of the present invention will be discussed along with a first embodiment of interconnection thereof. As shown in FIG. 3, the shaft 30 in accordance with the present invention is comprised of a plurality of links 31 connected together end to end to form the shaft 30. Each link 31 includes a female end 33 and a male end 35. As seen in FIG. 3, the female end 33 includes a slot 37 including a bottom wall 39 extending substantially perpendicularly to the longitudinal extent of the link 31, and a pair of sides 41 which are closest together at the end 43 of the link 31 and diverge from one another until arriving at the bottom wall 39.

With further reference to FIG. 3, it is seen that the male portion 35 of the link 31 includes a protruding member 45 which includes a top wall 47 also defining the uppermost portion of the link 31 and two sides 49 which are at their furthest distance from one another at the top wall 47 and converge toward one another until arriving at a shoulder formed by the walls 51. As may be seen from comparison of the recess 37 and the protruding member 45, the recess and protruding member are so designed that the protruding member 45 may be laterally slid into the recess 37 with the interaction between the respective walls 41 of the recess 37 and the walls 49 of the protruding member 45 preventing axial disengagement thereof.

The volume created by the recess 37 is slightly greater than the volume displaced by the protruding member 45 so that slight relative motion therebetween is possible to thereby enable the entire shaft 30 to be bent with respect to its normal straight longitudinal axis. However, the elongated nature of the recess 37 and the protruding member 45 in a direction perpendicular to the longitudinal axis of the links 31 causes the relative motion between the protruding members 45 and their respective recesses 37 to be extremely slight. Accordingly, when a link at a first end of the shaft 30 is twisted by means such as an electric rotary motor, torque is transmitted to a link at a second end of the shaft 30 substantially simultaneously and directly with virtually no lag therebetween. Accordingly, the shaft 30 of the present invention provides a direct interconnection between a drive means and a drill bit for effective intramedullar reaming.

With further reference to FIG. 3, it is seen that each link 31 includes extending longitudinally therethrough along the axis thereof, a hole 53. When several links are assembled together and longitudinally aligned, a continuous passageway is formed extending from a link at one end of the series of links to a link at a second end of the series of links. With further reference to FIGS. 3 and 10, it is seen that a first embodiment of interconnection of the links together comprises a flexible elongated rod 60 which may be inserted through the passageways 53 formed in the associated links 31 to thereby prevent disassembly of the links 31 comprising the shaft 30. Again, it is stressed, that the only way to disassemble the links 31 from one another is to slide them laterally with respect to one another to thereby disengage the protruding members 45 from the respective recesses 37. As may be seen in FIG. 3, the provision of the flexible rod 60 extending therethrough prevents such lateral movement and thereby prevents disassembly. If desired, the flexible rod 60 may be made of any flexible material such as rubber or plastic which will maintain its flexibility while not being broken by the links 31.

Figure 11:
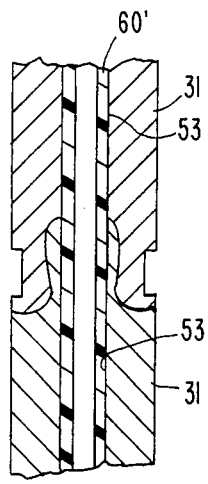
FIG. 11 shows a cross-sectional view corresponding to that of FIG. 10, but with an alternative link securement.

With further reference to FIG. 11, an alternative link ssecurement device may take the form of the tube 60' instead of the rod 60 shown in FIGS. 3 and 10. The tube 60' may be made of any flexible material such as rubber or plastic which will maintain its flexibility while not being broken by the links 31.

With reference now to FIG. 4, a second means for interconnecting the links 31 into a shaft 30 is shown. As shown in FIG. 4, after the links 31 are connected together, a flexible sleeve 70 may be fitted over the links 31 as assembled so as to again prevent relative lateral movement thereof and thereby assemble the links together into a shaft 30. The sleeve 70 may be made of any flexible material any should be sized so as to snugly fit over the exterior walls of the respective links 31. One advantageous way of assembling the sleeve 70 about the links 31 is to provide a sleeve 70 of slightly greater internal dimension than the external dimensions of the links 31 and to thereafter shrink-fit the sleeve 70 over the links 31 so as to complete the assembly. The sleeve 70 is a particularly advantageous means for assembling the links 31 into a shaft 30' since the sleeve 70 prevents any blood or body tissues from entering into spaces formed between the links 31. Accordingly, the shaft 31' formed in this manner is quite easy to sterilize for the purpose of re-use.

FIGS. 5 and 6 show side and cross-sectional views respectively of a third embodiment of reamer shaft designated by reference numeral 30". With reference first to FIG. 5, it is seen that the female end 33 of the upper link 31 is provided with a partial groove 57 and it is further seen that the male end 35 of the lower link member 31 is provided with a further partial groove means 59. When the protruding member 45 is assembled into the recess 37, these partial grooves 57 and 59 align with one another to form a continuous annular groove extending completely circumferentially of the two interengaged links 31. With this continuous groove being formed by the links 31, a ring 56 is deformed into the groove formed by the groove portions 57 and 59 to thereby prevent relative lateral movement of the links 31 to thereby prevent disassembly thereof. Such structure may be provided so as to assemble all of the links together to form a shaft 30".

As may be seen in FIG. 6, the groove as exemplified by groove portions 57 has a slightly longer longitudinal extent than the width of the ring 56 in the direction of the longitudinal axes of the links 31. Accordingly, this dimension difference allows the rings 56 to move slightly up and down along the longitudinal axes of the links 31. In this way, the slight movement between the respective protrusions 45 and recesses 37 as described hereinabove is permitted to thereby allow the bending of the reamer shaft 30" about its normal longitudinal axis while permitting direct torque transmission therethrough as also described hereinabove.

With reference now to FIGS. 7 and 8, a further means for connection of the links together will be described. FIG. 7 shows a portion of a shaft 30''' formed of links 31'. The links 31' differ from the links 31 in that the protruding members 45' thereof have slightly different construction. As seen in FIG. 7, the links 45' include protrusions 61 which extend laterally beyond the lateral extent of the female portion 33' of the associated link. Thus, in assembling the links together, the respective protrusions 45' are inserted into the respective recesses 37' until the respective links 31' are laterally aligned. Thereafter, with reference to FIG. 8, the lateral ends 61 of the protrusion 45' are deformed by a means such as a hammer so as to cause the ends 61 to flatten out. This flattening out of the ends 61 causes them to extend over the edges of the recess 37' to thereby prevent relative lateral movement therebetween. Accordingly, in this manner, the links 31' may be permanently assembled to one another in a manner that enables the links 31' to form a shaft 30''' which may bend with respect to its normal longitudinal axis while allowing direct transmission of torque from a drive means to a drill bit thereof.

With reference now to FIG. 9, a shaft 30 typical of the embodiments described hereinabove is shown with details of connection means thereof shown. With reference to FIG. 9, several links 31 may be joined together in one of the manners disclosed hereinabove to form an elongated reamer shaft 30. At a first end of the shaft 30, a link 31" is provided which includes a normal female end 33 but has its male end replaced with a cylindrical protrusion 63. The cylindrical protrusion 63 is provided so as to enable connection to a motor 65 via a motor shaft 67, a chuck 68 and a set screw 69 extending through the wall of the chuck 68 and engaging the outer surfaces of the cylindrical portions 63 to thereby drivingly interconnect the member 63 and the chuck 68.

With further reference to FIG. 9, it is seen that at the other end of the reamer shaft 30, a link 31''' is provided which includes the normal male end 35 but has its female end replaced with a connection means 71 including flat sides 73 having a substantially cylindrical member attached to the ends of the sides 73, with the axis of this cylindrical member 75 extending at right angles to the longitudinal extent of the link 31'''. A drill bit 77 is provided which includes a recess 78 corresponding to the protrusion formed by the walls 73 and cylindrical member 75 to thereby enable lateral movement of the bit 77 with respect to the link 31''' to thereby assembly the bit 77 to the link 31'''. Thereafter, a means such as a set screw 79 or other means known to those skilled in the art may be utilized to fix the drill bit 77 against relative movement with respect to the link 31'''.

It is noted that the cylindrical portion 63 and connection means 71 are designed so as to be utilized by chucks 68 and recesses 78 common in the art so as to enable universal application of the teachings of the present invention.

It is further noted, that if desired, the reamer shaft 30 shown in FIG. 9 may be configured so that the link 31'' includes a male end and the link 31''' includes a female end as desired.

Thus, a reamer shaft has been designed having links thereof made of lengths and diameters selected to allow optimization of the flexibility of the shaft along its longitudinal axis while maintaining the necessary torsional strength. Various modifications, alterations, or changes may be made to the teachings disclosed hereinabove without departing from the intent of the present invention. For example, if desired, the flexible rod 60 and the sleeve 70 may be made of flexible metallic materials or any other material which will act to assemble the links 31 together while allowing the desired flexibility therebetween. Further, the members 63 and 71 may be made of any configuration as desired so as to enable connection of the reamer shaft 30 to the appropriate drive means and drill bit. It is noted that the term "drill bit" is considered to be interchangeable with the term "reamer head" for the purposes of this disclosure. While the invention disclosed herein is not considered to be directly concerned with the methods of reaming the intramedullary canals, it is noted that the present invention is easily usable in conjunction with an appropriate guide wire previously introduced into the intramedullary canal of the bone being reamed as is well known to those skilled in the art. Accordingly, it is to be understood that the present invention should only be limited by the terms of the appended claims.

I claim:

1. A flexible connecting shaft for an intramedullary canal reamer, comprising:
   (a) first link means including first connection means for connecting said first link means to drive means;
   (b) second link means including second connection means for connecting said second link means to reamer head means; and
   (c) further link means interconnecting said first and second link means and including:
      (1) a male end adapted to interfit with a female end formed on one of said first link means and said second link means;
      (2) a female end adapted to interfit with a male end formed on the other of said first link means and said second link means;
      (3) said shaft including fastening means for preventing disconnection of said link means;
   (d) said shaft having a longitudinal axis and said link means interacting through structure allowing flexing of said shaft about said axis while substantially preventing relative twisting of any one link means with respect to any other link means, whereby said shaft may directly transmit torque from said drive means to said reamer head means substantially without slippage while said shaft conforms to the specific shape of the canal; said structure including:
      (1) each said female end including a slot extending substantially perpendicular to said axis and having a narrowed opening;
      (2) each said male end including a protruding member substantially corresponding, in shape, to the shape of said slot but of slightly smaller volume;
      (3) said protruding member being insertable into a respective slot in a direction substantially perpendicular to said axis and being constrained from removal axially by said narrowed opening; and
   (e) further wherein said fastening means comprises:
      (1) each link means including a longitudinal passageway therethrough; and
      (2) flexible rod means extending through the passageways in all said link means.

2. The invention of claim 1, wherein said further link means comprises a plurality of interconnected links.

3. The invention of claim 1, wherein said further link means includes a plurality of links, each said link including one said male end and one said female end.

4. A flexible connecting shaft for an intramedullary canal reamer, comprising:
   (a) first link means including first connection means for connecting said first link means to drive means;
   (b) second link means including second connection means for connecting said second link means to reamer head means; and
   (c) further link means interconnecting said first and second link means and including:
      (1) a male end adapted to interfit with a female end formed on one of said first link means and said second link means;
      (2) a female end adapted to interfit with a male end formed on the other of said first link means and said second link means;
      (3) said shaft including fastening means for preventing disconnection of said link means;
   (d) said shaft having a longitudinal axis and said link means interacting to allow flexing of said shaft about said axis while substantially preventing relative twisting of any one link means with respect to any other link means, whereby said shaft may directly transmit torque from said drive means to said reamer head means substantially without slippage while said shaft conforms to the specific shape of said canal; and
   (e) further wherein said fastening means comprises;
      (1) each link means including a longitudinal passageway therethrough; and
      (2) flexible plastic tube means extending through the passageways in all said link means.

* * * * *